US006423737B2

(12) United States Patent
Hall et al.

(10) Patent No.: US 6,423,737 B2
(45) Date of Patent: *Jul. 23, 2002

(54) BENZAMIDOXIME PRODRUGS AS ANTIPNEUMOCYSTIC AGENTS

(75) Inventors: James E. Hall, Chapel Hill; Richard R. Tidwell, Pittsboro, both of NC (US); David W. Boykin, Atlanta, GA (US)

(73) Assignees: The University of North Carolina at Chapel Hill, Chapel Hill, NC (US); Georgia State University Research Foundation, Inc., Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/759,664

(22) Filed: Jan. 12, 2001

Related U.S. Application Data

(60) Division of application No. 09/477,390, filed on Jan. 4, 2000, now Pat. No. 6,214,883, which is a division of application No. 09/127,317, filed on Jul. 31, 1998, now Pat. No. 6,025,398, which is a division of application No. 08/751,171, filed on Nov. 15, 1996, now Pat. No. 5,843,980, which is a continuation-in-part of application No. 08/558,716, filed on Nov. 16, 1995, now Pat. No. 5,723,495.

(51) Int. Cl.[7] .................. A61K 31/15; A61K 31/155
(52) U.S. Cl. .................. 514/399; 514/438; 514/471; 514/633
(58) Field of Search .................. 514/399, 438, 514/471, 633

(56) References Cited

U.S. PATENT DOCUMENTS

| | | | |
|---|---|---|---|
| 2,425,223 A | 8/1947 | Barber | 260/501 |
| 2,449,724 A | 9/1948 | Short et al. | 260/564 |
| 2,851,495 A | 9/1958 | Jensch et al. | 260/564 |
| 3,767,616 A | 10/1973 | Zellner | 260/47 |
| 4,034,010 A | 7/1977 | Hamano et al. | 260/564 |
| 4,064,169 A | 12/1977 | Hamano et al. | 260/564 |
| 4,237,168 A | 12/1980 | Reifschneider | 424/326 |
| 4,546,113 A | 10/1985 | Glazer | 514/636 |
| 4,933,347 A | 6/1990 | Tidwell et al. | 514/256 |
| 5,262,157 A | 11/1993 | Bernard et al. | 424/45 |
| 5,364,615 A | 11/1994 | Debs et al. | 424/45 |
| 5,366,726 A | 11/1994 | Debs et al. | 424/45 |
| 5,786,383 A | 7/1998 | Clement | 514/633 |

FOREIGN PATENT DOCUMENTS

| | | |
|---|---|---|
| EP | 0 366 066 A1 | 10/1989 |
| FR | 2.081.401 | 12/1971 |
| WO | WO 94/08580 | 4/1994 |
| WO | WO 95/01168 | 1/1995 |
| WO | WO 95/08540 | 3/1995 |

OTHER PUBLICATIONS

B. Clement et al.; Amidoximes of Pentamidine: Synthesis, Trypanocidal and Leishmanicidal Activity, *Arzneim–Forsch/Drug Res.* 35(II), Nr. 7: 1009–1014 (1985).

B. Clement et al.; Reduction of Amidoxime Derivatives to Pentamidine in vivo, *Arch. Pharm. (Weinheim)* 325: 61–62 (1992).

B. Clement et al.; N–Hydroxylation of the Antiprotozoal Drug Pentamidine Catalyzed by Rabbit Liver Cytochrome P–450 2C3 or Human Liver Microsomes, Microsomal Retroreduction, and Further Oxidative Transformation of the Formed Amidoximes, *Drug Metabolism and Disposition* 22:486–497 (1994).

A.T. Fuller et al.; Chemotherapeutic Agents if the Sulphone Type. Part II. Sulphones Related to Benzamidine and Benzylamine, *J. Chem. Soc.* 633–640 (1945).

C.H. Andrewes et al.; Experimental chemotherapy of typhus. Anti–rickettsial action of p–sulphonamidobenzamidine and related compounds, *Proc. Royal Soc.* (London) 133B:20–62 (1946).

N.P. Buu–Hoi et al.; Une nouvelle famille de composes tuberculostatiques: les amidoximes, *Experientia* 10:169 (1954).

P. Chabrier et al.; Nouvelles recherches sur les rapports entre structure chimique, activite' antibacterienne, antifungique' et toxicite', dans la serie des esters de l'acide dithiocarbamique N–disubstitue', *Ann. Pharm. Franc.* 14:720–728 (1956).

I.D. Lamb et al.; Some Amidines and Amidoximes with Trypanocidal Activity, *J. Chem. Soc.* 1253–1257 (1939).

David W. Boykin et al.; Dicationic Diarylfurans as Anti–Pneumocysis carinii Agents, *J. Med. Chem.*, 38:912–916(1995).

P M S Chauhan et al.; Synthesis of 2,8–Diamidinodibenz [b,f]oxepin & Related Compounds as Potential Leishmanicides, *Indian Journal of Chemistry*, 22B:898–900 (Sep. 1983).

P M S Chauhan et al.; Antiparasitic Agents: Part VI.— Synthesis of 1,2–,13–& 4,4–Bis(4–substituted aryloxy)benzenes & Their Biological Activities, *Indian Journal of Chemistry*, 27B:38–42 (Jan 1988).

Clement et al.; Metabolic N–Hydroxylation of Diminazene in vitro, *Arzneim.–Forsch./Drug Res.*, 42(II), Nr. 12:1497–1504 (1992).

*Primary Examiner*—Richard L. Raymond
(74) *Attorney, Agent, or Firm*—Jenkins & Wilson, P.A.

(57) ABSTRACT

A method of treating *Pneumocystis carinii* pneumonia in a subject in need of such treatment is disclosed. The method comprises orally administering to the subject a bis-benzamidoxime, or a pharmaceutically acceptable salt thereof, that is reduced in the subject to produce a benzamidine having anti-*P. carinii* activity. The method of the present invention may alternatively comprise intravenously administering to the subject an active compound as disclosed herein. Pharmaceutical formulations and active compounds useful in the practice of the present invention are also disclosed.

9 Claims, 4 Drawing Sheets

US 6,423,737 B2

BENZAMIDOXIME PRODRUGS AS ANTIPNEUMOCYSTIC AGENTS

RELATED APPLICATIONS

This application is a divisional of U.S. application Ser. No. 09/477,390, filed Jan. 4, 2000, now U.S. Pat. No. 6,214,883; which is a divisional of U.S. application Ser. No. 09/127,317, filed Jul. 31, 1998, now U.S. Pat. No. 6,025,398; which is a divisional of U.S. application Ser. No. 08/751,171, filed Nov. 15, 1996, now U.S. Pat. No. 5,843,980; which is a continuation-in-part of U.S. application Ser. No. 08/558,716, filed Nov. 16, 1995, now U.S. Pat. No. 5,723,495.

The present invention was made with Government support under Grant Number 5-UO1-AI33363-03 from the National Institutes of Health. The Government has certain rights to this invention.

FIELD OF THE INVENTION

The present invention relates to methods useful in combating *Pneumocystis carinii* pneumonia and prodrug compounds useful therefor.

BACKGROUND OF THE INVENTION

Pentamidine is used for the treatment of *Pneumocystis carinii* pneumonia, or "PCP". The importance of pentamidine has dramatically escalated recently due to the marked increase of patients suffering from PCP. The increase in the afflicted patient population is an unfortunate consequence of the increasing presence of the Acquired Immunodeficiency Syndrome ("AIDS"). It is now estimated that approximately 70 percent of AIDS patients contract PCP. Because of the high incidence of PCP in AIDS patients, pentamidine has found utility not only in the treatment of PCP, but also as prophylaxis, in preventing or delaying the initial onset or recurrence of PCP, especially in AIDS patients. Currently, pentamidine is most commonly administered as a therapeutic agent by intravenous infusion and as a prophylactic agent by aerosol dosage.

However, an unfortunate side effect of pentamidine is its toxicity. Some fatalities have been attributed to severe hypotension, dysglycemia, and cardiac arrhythmias in patients treated with pentamidine. Contrawise, insufficient dosage may result in dissemination of disease beyond the lung, an occurrence which is associated with a poor prognosis. Therapeutic drug monitoring is not used because of the cost and complexity of the currently available assay techniques which require the extraction of plasma and High Performance Liquid Chromatography (HPLC) analysis. As a result, the toxicity of pentamidine is a significant concern, which is driving the market toward the development of pentamidine substitutes capable of avoiding or minimizing the undesirable side effects associated with the use of pentamidine. See, e.g., J. Spychala et al., *Eur. J. Med. Chem.* 29, 363–367 (1994); I. O. Donkor et al., *J. Med. Chem.* 37, 4554–4557 (1994); R. R. Tidwell et al., *J. Protozool.* 6, 148S–150S (1991).

Accordingly, it is an object of the present invention to provide new compounds useful in the treatment of *P. carinii* pneumonia.

SUMMARY OF THE INVENTION

A method of treating *Pneumocystis carinii* pneumonia in a subject in need of such treatment is disclosed. The method comprises orally administering to the subject a bis-benzamidoxime, derivative thereof, or a pharmaceutically acceptable salt thereof (hereinafter referred to as the "active compound"), that is reduced in the subject to produce a benzamidine having anti-*P. carinii* activity. The method of the present invention may alternatively comprise intravenously administering to the subject an active compound as disclosed herein.

A second aspect of the present invention is a pharmaceutical formulation comprising, in combination with a pharmaceutically acceptable carrier, a bis-benzamidoxime, or a pharmaceutically acceptable salt thereof, that is reduced in a mammalian subject after administration thereto to produce a benzamidine having anti-*Pneumocystis carinii* activity, subject to the proviso that said bis-benzamidoxime is not 1,5-bis(4'-(N-hydroxyamidino)phenoxy) pentane.

A third aspect of the present invention are active compounds useful in carrying out a therapeutic method of the present invention.

A fourth aspect of the present invention is the use of an active compound as disclosed herein for the manufacture of a medicament useful in carrying out a therapeutic method of treatment as given above.

BRIEF DESCRIPTION OF THE DRAWINGS

FIG. 1A illustrates the metabolism of compound 1 into its amidine analog pentamidine (indicated in the Figure by the numeral 2) and its monoamidine-monoamidoxime derivative (indicated in the Figure by the numeral 9).

FIG. 1B illustrates the metabolism of compound 3 into its amidine analog (indicated in the Figure by the numeral 4).

FIG. 1C illustrates the metabolism of compound5 into its amidine analog (indicated in the Figure by the numeral 6).

FIG. 1D illustrates the metabolism of compound 7 into its amidine analog (indicated in the Figure by the numeral 8).

FIG. 4A illustrates the metabolism of compound 1 into its amidine analog pentamidine (indicated in the Figure by the numeral 2) and its monoamidine-monoamidoxime derivative (indicated in the Figure by the numeral 9).

FIG. 4B illustrates the metabolism of compound 3 into its amidine analog (indicated in the Figure by the numeral 4).

FIG. 4C illustrates the metabolism of compound 5 into its amidine analog (indicated in the Figure by the numeral 6).

FIG. 4D illustrates the metabolism of compound 7 into its amidine analog (indicated in the Figure by the numeral 8).

DETAILED DESCRIPTION OF THE INVENTION

Figure 1:
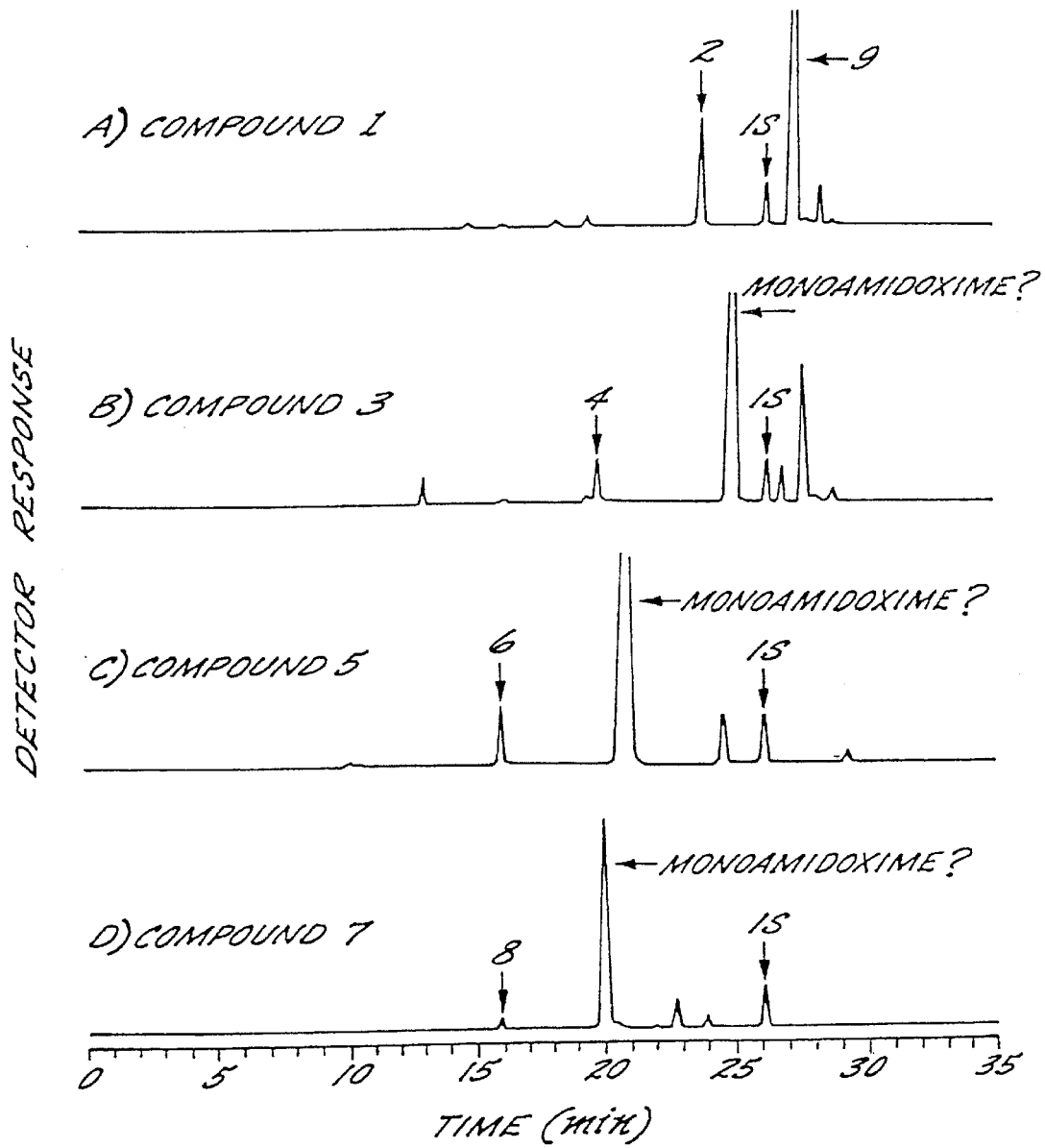
FIG. 1 is a spectral illustration of the metabolism of bis-benzamidoximes of the present invention by rat liver homogenate 9000×g supernatant fraction. In the metabolism studies illustrated in FIGS. 1A, 1B, 1C, and 1D, homgenates containing 167 $\mu$M test compound as substrate plus a cofactor solution were incubated at $37_E$C for 10 minutes, then assayed by HPLC as described below in Example 7. In all Figures, "IS" means internal standard.

Active compounds of the present invention are, in general, the bis-benzamidoxime derivatives of benzamidines that have anti-*Pneumocystis carinii* activity. The benzamidines having anti-*P. carinii* activity may be mono-benzamidines, wherein one amidoxime group of the bis-benzamidoxime derivative is reduced; alternatively, they may be bis-benzamidines wherein both amidoxime groups of the bis-benzamidoxime derivative are reduced. Thus, bis-benzamidoxime derivatives of benzamidines having anti-*P. carinii* activity are an aspect of the present invention. Examples of such benzamidines are disclosed in, e.g., U.S. Pat. No. 2,277,861 to Ewins et al.; U.S. Pat. No. 2,410,796 to Newberry et al.; U.S. Pat. No. 4,933,347 to Tidwell et al.; and PCT Application No. US93/09477 (applicant specifically intends the disclosure of these and all other patent references cited herein to be incorporated herein by reference).

As used herein, the term "cycloalkyl" as used herein refers to C3 to C6 cyclic alkyl, such as cyclopropyl, cyclobutyl, cyclopentyl, and cyclohexyl. Cyclohexyl and cyclopentyl are currently preferred. The term "aryl" as used herein refers to C3 to C10 cyclic aromatic groups such as phenyl, naphthyl, and the like, and includes substituted aryl groups such as tolyl. The term "hydroxyalkyl" as used herein refers to C1 to C4 linear or branched hydroxy-substituted alkyl, i.e., —$CH_2OH$, —$(CH_2)_2OH$, etc. The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —$NH_2$, —$NHCH_3$, —$N(CH_3)_2$, etc. The term "oxyalkyl" as used herein refers to C1 to C4 oxygen-substituted alkyl, i.e., —$OCH_3$, and the term "oxyaryl" as used herein refers to C3 to C10 oxygen-substituted cyclic aromatic groups.

One preferred group of compounds useful in the practice of the present invention are bis-benzamidoximes of the formula I:

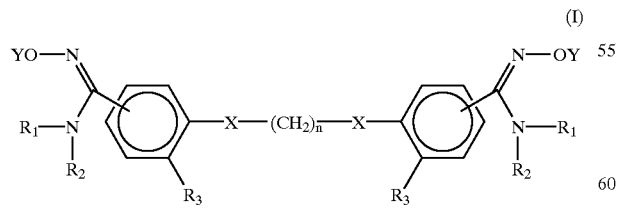

(I)

wherein:
R$_1$ and R$_2$ are each independently selected from the group consisting of H, loweralkyl, oxyalkyl, alkoxyalkyl, cycloalkyl, aryl, hydroxyalkyl, aminoalkyl or alkylaminoalkyl;

R$_3$ is H, loweralkyl, oxyalkyl, alkoxyalkyl, hydroxyalkyl, cycloalkyl, aryl, aminoalkyl, alkylaminoalkyl or halogen;

n is from 2 to 6;

X is O or S; and

Y is H or loweralkyl;

or pharmaceutically acceptable salts thereof.

A second preferred group of compounds useful in the practice of the present invention are bis-benzamidoximes of the formula II:

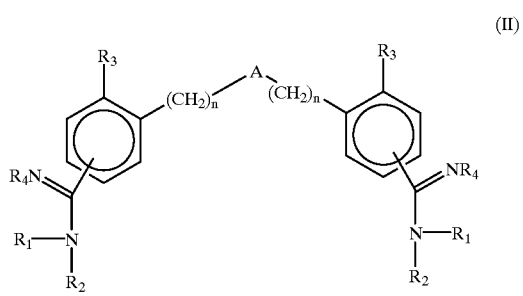

(II)

wherein:
R$_1$ and R$_2$ are each independently selected from the group consisting of H, loweralkyl, oxyalkyl, alkoxyalkyl, cycloalkyl, aryl, hydroxyalkyl, aminoalkyl or alkylaminoalkyl;

R$_3$ is H, loweralkyl, oxyalkyl, alkoxyalkyl, hydroxyalkyl, cycloalkyl, aryl, aminoalkyl, alkylaminoalkyl or halogen;

R$_4$ is —OY, or R$_1$ and R$_4$ together represent

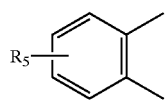

wherein R$_5$ is

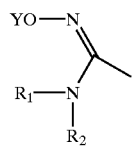

Y is H or loweralkyl;
n is an integer from 0 to 2; and
A is a heterocyclic aromatic group selected from the group consisting of:

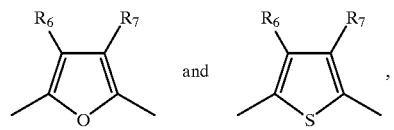

wherein R$_6$ and R$_7$ are each independently selected from the group consisting of H, loweralkyl, halogen, oxyalkyl, oxyaryl, or oxyarylalkyl;

or pharmaceutically acceptable salts thereof.

As noted above, the methods of the present invention are useful for treating *P. carinii* pneumonia. The methods of the present invention are useful for treating these conditions in that they inhibit the onset, growth, or spread of the condition, cause regression of the condition, cure the condition, or otherwise improve the general well-being of a subject inflicted with, or at risk of contracting the condition.

Subjects to be treated by the methods of the present invention are typically human subjects, although the methods of the present invention may be useful with any suitable subject known to those skilled in the art.

As noted above, the present invention provides pharmaceutical formulations comprising the aforementioned active compounds, or pharmaceutically acceptable salts thereof, in pharmaceutically acceptable carriers for oral, intravenous, or aerosol administration as discussed in greater detail below.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 100 mg/kg will have therapeutic efficacy, with all weights being calculated based upon the weight of the active base, including the cases where a salt is employed. A dosage from about 10 mg/kg to about 50 mg/kg may be employed for oral administration. The duration of the treatment is usually once per day for a period of two to three weeks or until the $P.$ $carinii$ pneumonia is essentially controlled. Lower doses given less frequently can be used to prevent or reduce the incidence of recurrence of the infection.

In accordance with the present method, an active compound as described herein, or a pharmaceutically acceptable salt thereof, may be administered orally as a solid or as a liquid, or may be administered intravenously. Alternatively, the active compound or salt may also be administered by inhalation. When administered through inhalation the active compound or salt should be in the form of a plurality of solid particles or droplets having a particle size from about 0.5 to about 5 microns, preferably from about 1 to about 2 microns.

Besides providing a method for treating $P.$ $carinii$ pneumonia, the active compounds of the present invention also provide a method for prophylaxis against $P.$ $carinii$ pneumonia in an immunocompromised patient, such as one suffering from AIDS, who has had at least one episode of $P.$ $carinii$ pneumonia, but who at the time of treatment is not exhibiting signs of pneumonia. As $P.$ $carinii$ pneumonia is an especially potentially devastating disease for immunocompromised patients it is preferable to avoid the onset of $P.$ $carinii$ pneumonia, as compared to treating the disease after it has become symptomatic. Accordingly, the present invention provides a method for the prophylaxis against $P.$ $carinii$ pneumonia comprising administering to the patient a prophylactically effective amount of the active compound or a pharmaceutically acceptable salt thereof. The forms for administration of the compound or salt in accordance with this method may be the same as utilized for the purpose of actually treating a patient suffering from $P.$ $carinii$ pneumonia.

An additional useful aspect of the present invention is a method for prophylaxis against even an initial episode of $P.$ $carinii$ pneumonia in an immunocompromised patient who has never experienced an episode of $P.$ $carinii$ pneumonia. In this respect, a patient who has been diagnosed as being immunocompromised, such as one suffering from AIDS or ARC (AIDS related complex), even before the onset of an initial episode of $P.$ $carinii$ pneumonia, may avoid or delay suffering from the infection by having administered a prophylactically effective amount of an active compound of the present invention or a pharmaceutically acceptable salt thereof. The compound or salt may be administered in the same fashion as in the treatment of patients suffering from $P.$ $carinii$ pneumonia.

In the manufacture of a medicament according to the invention (a "formulation"), active agents or the pharmaceutically acceptable salts thereof (the "active compound") are typically admixed with, inter alia, an acceptable carrier. The carrier must, of course, be acceptable in the sense of being compatible with any other ingredients in the formulation and must not be deleterious to the subject. The carrier may be solid or liquid, or both, and is preferably formulated with the compound as a unit-dose formulation, for example, a tablet, which may contain from 0.05% to 99% by weight of the active compound. One or more active compounds may be incorporated in the formulations of the invention (e.g. the formulation may contain one or more additional anti-$P.$ $carinii$ agents as noted above), which formulations may be prepared by any of the well-known techniques if pharmacy consisting essentially of admixing the components, including one or more accessory therapeutic ingredients.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations for oral administration may optionally include enteric coatings known in the art to prevent degradation of the formulation in the stomach and provide release of the drug in the small intestine.

In addition to the active compounds or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Other pharmaceutical compositions may be prepared from the water-insoluble active compounds, or salts thereof, such as aqueous base emulsions. In such an instance, the composition will contain a sufficient amount of pharmaceutically acceptable emulsifying agent to emulsify the desired amount of the active compound or salt thereof. Particularly useful emulsifying agents include phosphatidyl cholines, and lecithin.

Further, the present invention provides liposomal formulations of the active compounds and salts thereof. The technology for forming liposomal suspensions is well known in the art. When the active compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the active compounds or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired active compound or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid active compound, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble active compound of the present invention or a salt thereof, in a carrier which comprises water. A surfactant may be present which lowers the surface tension of the formulation sufficiently to result in the formation of droplets within the desired size range when subjected to nebulization.

Formulations of the present invention suitable for intravenous administration comprise sterile aqueous and non-aqueous injection preparations of the active compound, which preparations are preferably isotonic with the blood of the intended recipient. These preparations may include antioxidants, buffers, bacteriostats, and solutes that render the formulation isotonic with the blood of the intended recipient. Aqueous and non-aqueous sterile suspensions may include suspending agents and thickening agents. The formulations may be presented in unit/dose or multi-dose containers, for example sealed ampules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

As indicated, the present invention provides both water-soluble and water-insoluble compounds and salts. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

Examples of active compounds of the present invention include, but are not limited to:

X 1,3-bis(4'-(N-hydroxyamidino)phenoxy)propane
X 1,3-bis(2'-methoxy-4'-(N-hydroxyamidino)phenoxy) propane
X 1,4-bis(4'-(N-hydroxyamidino)phenoxy)butane
X 1,3-bis(4'-(4-hydroxyamidino)phenoxy)propane di-hemimaleinate
X 1,3-bis(2'-methoxy-4'-(N-hydroxyamidino)phenoxy) propane di-hemimaleinate
X 1-(4'-(N-hydroxyamidino)phenoxy)butane bis-maleinate
X 2,5-bis-[4-amidinophenyl]furan bis-amidoxime
X 2,5-bis-[4-amidinophenyl]furan bis-O-methylamidoxime
X 2,5-bis-[4-amidinophenyl]furan bis-O-ethylamidoxime Compounds employed in carrying out the present invention may be prepared in accordance with techniques known to those skilled in the art, particularly in light of the disclosure and examples set forth below.

As indicated, the compounds used in the present invention may be present as pharmaceutically acceptable salts. Such salts include the maleinate, gluconate, lactate, acetate, tartarate, citrate, phosphate, borate, nitrate, sulfate, and hydrochloride salts.

The salts of the present invention may be prepared, in general, by reacting two equivalents of the pyrimidine base compound with the desired acid, in solution. After the reaction is complete, the salts are crystallized from solution by the addition of an appropriate amount of solvent in which the salt is insoluble.

As noted above, the active compounds of the present invention according to Formula I may be prepared according to methods known in the art. For example, the active compounds above may be prepared by first synthesizing known bis-nitriles using Allen's procedure for alkylation of phenols. See J. N. Ashley et al., *J. Chem. Soc.* 103–116 (1942); C. F. H. Allen et al. *Org. Synth. Coll.* III, 141-41 (1955). The active compounds can then be obtained by using variations of the known technique of Clement and Raether and by using appropriate reagents. See B. Clement and W. Raether, *Arzneim. Forsch.* 35, 1009–1014 (1985).

Active compounds of the present invention according to Formula II may also be produced by methods known in the art. For example, a two-step process using Pinner methodology may be used to convert a nitrile into an imidate ester, followed by reaction of the imidate ester with hydroxylamine. A. Pinner, *Ber.* 17, 184 (1884). Alternatively, amidoximes according to Formula II may be prepared by the direct conversion of a nitrile into the amidoxime by the reaction with hydroxylamine in the presence of base. I. Lamb et al., *J. Chem. Soc.* 1253 (1939).

Subjects with other microbial infections, in addition to *P. carinii* pneumonia, may also be treated by the methods of the present invention in the same manner as described above. These infections may be caused by a variety of microbes, including fungi, algae, protozoa, bacteria, and viruses. Exemplary microbial infections that may be treated by the method of the present invention include, but are not limited to, infections caused by *Giardia lamblia, Cryptosporidium parvum, Cryptococcus neoformans, Candida albicans, Candida tropicalis, Salmonella typhimurium, Plasmodium falciparum,* and *Leishmania mexicana amazonensis.*

The following examples are provided to illustrate the present invention, and should not be construed as limiting thereon. In these examples, mM means millimolar, mL means milliliters, mm means millimeters, cm means centimeters, $_EC$ means degrees Celsius, g means grams, kg means kilograms, m.p. means melting point, MHz means megahertz, M means molar, h means hours, NMR means nuclear magnetic resonance, FAB means fast atom bombardment, DMF means dimethylformamide, EtOH means ethyl alcohol, DMSO means dimethylsulfoxide, HPLC means high-pressure liquid chromatography, TLC means thin-layer chromatography, dec means decomposition point.

In the following Examples, the following compound designations are used throughout.

| Compound# | Name |
|---|---|
| a | 1,5-bis(4'-(N-hydroxyamidino)phenoxy)pentane |
| b | 1,3-bis(4'-(N-hydroxyamidino)phenoxy)propane |
| c | 1,3-bis(2'-methoxy-4'-(N-hydroxyamidino)phenoxy)propane |
| d | 1,4-bis(4'-(N-hydroxyamidino)phenoxy)butane |
| 1 | 1,5-bis(4'-(N-hydroxyamidino)phenoxy)pentanedi-hemimaleinate |
| 2 | 1,5-bis(4'-amidinophenoxy)pentane; pentamidine |
| 3 | 1,4-bis(4'-(N-hydroxyamidino)phenoxy)butanedi-maleinate |
| 4 | 1,4-bis(4'-amidinophenoxy)butane |
| 5 | 1,3-bis(4'-(4-hydroxyamidino)phenoxy)propanedi-hemimaleinate |
| 6 | 1,3-bis(4'-amidinophenoxy)propane |
| 7 | 1,3-bis(2'-methoxy-4'-(N-hydroxyamidino)phenoxy)propanedi-hemimaleinate |
| 8 | 1,3-bis(2'-methoxy-4'-amidinophenoxy)propane |
| 9 | 2,5-bis-[4-amidinophenyl]furan |
| 10 | 2,5-bis-[4-amidinophenyl]furanbis-amidoxime |
| 11 | 2,5-bis-[4-amidinophenyl]furanbis-O-methylamidoxime |
| 12 | 2,5-bis-[4-amidinophenyl]furanbis-O-ethylamidoxime |

EXAMPLE 1

Synthesis of Formula I Compounds: Preparation of bis-benzonitriles 42 mmol of 1,5-dibromopentane (for preparing pentamidine derivatives) or 1,3-dibromopentane (for preparing propamidine derivatives) is added to a suspension of 84 mmol of the appropriate 4-hydroxybenzonitrile and 126 mmol of $K_2CO_3$ in 200 mL DMF. The mixture is warmed to 65–70$_E$C and allowed to stir overnight. The mixture is diluted in 400 mL of $H_2O$, the precipitated product is collected and washed with $H_2O$. The crude bis-benzonitriles are recrystallized from ethanol.

EXAMPLE 2

Synthesis of Formula I Compounds: Preparation bis-benzamidoximes 32 mL of a 21% sodium ethoxide (in ethanol) solution is added to a hot solution of 98 mmol of $NH_2OH_X HCl$ in 100 mL ethanol. The NaCl is removed by filtration and the filtrate is entered directly into a flask containing 10 mmol of the appropriate bis-benzonitrile from Example 1. The mixture is warmed to reflux and allowed to stir for 5 hrs, cooled to room temperature and permitted to stand overnight. The precipitated product is collected, washed with ethanol and dried in a vacuum desiccator. The following spectral and analytic data were collected:

Compound (a): m.p.>164-65$_E$C; (literature value: 163$_E$C; see R. R. Tidwell et al., *J. Med Chem.* 26, 294-98 (1983)); 3.6 g, 60%.

Novel Compound (b): m.p. 162$_E$C, (1.6 g, 47%); $^1$H-NMR (300 MHz, DMSO) δ 2.18 (m, 2 H), 4.16 (t, J=5.9 Hz, 4 H), 5.72 (s, 4 H), 6.95 (d, 4 H, J=8.6 Hz), 7.59 (d, 4 H, J=8.6 Hz), 9.45 (s, 2 H) ppm; FABMS m/z 345 (M+H); Exact mass calculated for $C_{17}H_{21}N_{14}O_4$: 345.1563; found: 345.1557; Anal. $(C_{17}H_{21}N_{14}O_4)$: C, H, N.

Novel Compound (c): m.p.117$_E$C (2.9 g, 73%); $^1$H-NMR (300 MHz, DMSO) δ 2.17 (m, 2 H), 4.14 (t, 4 H, J=5.9 Hz), 5.74 (s, 4 H), 6.98 (d, 2 H, J=8.4 Hz), 9.46 (s, 2 H) ppm; FABMS m/z 405 (M+H); Exact mass calculated for $C_{19}H_{25}N_4O_6$: 405.1774; found: 405.1795; Anal. $(C_{19}H_{25}N_4O_6 X (H_2O)_{1.3}$: C, H, N.

Novel Compound (d): m.p.200$_E$C (dec) (1.0 g, 33%); $^1$H-NMR (300 MHz, DMSO) δ 1.87 (s, 2 H), 4.05 (s, 2 H), 5.72 (s, 4 H), 6.95 (d, 4 H, J=8.7 Hz), 7.60 (d, 2 H, J=8.7 Hz), 9.45 (s, 2 H) ppm; FABMS m/z 359 (M+H); Anal. $(C_{18}H_{22}N_4O_4)$: C, H, N.

Further elemental analysis data is shown in Table 1.

TABLE 1

Elemental Analyses of Novel Amidoximes

| Compound | Molecular Formula | Calculated | Found |
|---|---|---|---|
| b | $C_{17}H_{20}N_4O_4$ | C:59.30; H:5.81; N:16.28 | C:59.12; H:5.86; N:16.00 |
| c | $C_{19}H_{24}N_4O_6 X(H_2O)_{1.3}$ | C:53.34; H:6.27; N:13.10 | C:53.64; H:6.01; N:12.71 |

TABLE 1-continued

Elemental Analyses of Novel Amidoximes

| Compound | Molecular Formula | Calculated | Found |
|---|---|---|---|
| d | $C_{18}H_{22}N_4O_4$ | C:59.13; H:6.29; N:15.32 | C:59.75; H:6.24; N:14.67 |
| 3 | $C_{18}H_{22}N_4O_4 X1.60 C_4H_4O_4$ | C:58.21; H:6.65; N:12.93 | C:57.99; H:6.55; N:13.29 |
| 5 | $C_{25}H_{28}N_4O_{12}X(H_2O)_{1.6}$ | C:49.59; H:5.20; N:9.26 | C:49.39; H:4.99; N:9.59 |
| 7 | $C_{27}H_{32}N_4O_{14}X(H_2O)$ | C:49.53; H:5.26; N:10.30 | C:53.88; H:5.31; N:10.03 |

EXAMPLE 3

Synthesis of Formula I Compounds: Preparation of maleinate salts of bis-benzamidoxime compounds 2.7 mmol of the appropriate bis-amidoxime of Example 2 was taken up in 20 mL hot THF. Insoluble impurities (monoadducts) are removed by addition of 20 mL of a THF solution of either 6.8 mmol or 3.6 mmol of maleic acid. The resulting precipitate is collected and washed with ether/ethanol and then ether to give the bis-hemimaleinates as colorless powders in most cases. The following analytical and spectral data are observed:
Compound (1): m.p. 118–120$_E$C (literature 115–120$_E$C, see R. R. Tidwell et al., *J. Med Chem.* 26, 294-98 (1983)), (1.2 g, 75%).
Novel Compound (3): m.p. 154$_E$C (1.1 g, 67%) Anal. [$C_{18}H_{22}N_4O_4$ (C,H,N).
Novel Compound (5): m.p. 135$_E$C (dec) (800 mg, 91%); Anal. ($C_{25}H_{28}N_4O_{12}X(H_2O)_{1.6}$) C,H,N.
Novel Compound (7): m.p. 134$_E$C (dec) (700 mg, 86%) Anal. [$C_{27}H_{32}N_4O_{14}X$ ($H_2O$)] C, H, N.
Further elemental analysis data is shown in Table 1.

EXAMPLE 4

Activity of Novel Compounds of Formula I Against *Pneumocystis carinii*

The activity of the compounds of Formula I against *P. carinii* was carried out according to an established method. See Tidwell, R. R., et al., *J. Protozool.* 36, 74S–76S (1989); Jones, S. K., et al., *Antimicrob. Agents Chemother.* 34, 1026–1030 (1990); Tidwell, R. R., et al., *Antimicrob. Agents Chemother.* 37, 1713–1716 (1993). Briefly, male Sprague-Dawley rats (barrier raised, not certified virus-free) weighing 150–200 g each, were obtained (Hilltop Laboratories, Scottsdale, Pa.). Immediately upon arrival, the animals were caged individually and begun on a low protein (8%) diet and on drinking water containing tetracycline (0.5 mg/mL) and dexamethasone (1.0 $\mu$/mL). This regimen was continued for eight weeks. At the beginning of the seventh week, animals were divided into groups of 8 or more, and the test compounds were administered for 14 days. Saline and pentamidine-treated groups were included as controls.

Animals were sacrificed at the end of the eighth week by chloroform inhalation. The left lung was weighed, ground through a No. 60 wire mesh screen, and suspended 1:10 (wt/vol) in 10 mM β-mercaptoethanol-Hanks' balanced salts solution (HBSS) without cations. Slides were prepared by spotting 5 $\mu$L of lung homogenate diluted 1:10 in HBSS with β-mercaptoethanol and allowed to air dry. The slides were stained with cresyl violet, and the cysts were counted by a blinded protocol. The number of cysts per gram of original lung tissue was calculated, and the groups were reported as the percentages of saline-treated controls.

The anti-*P. carinii* value for each compound is expressed as the percent of cysts in the treatment group as compared to the saline control group. Values are also compared to a positive control group consisting of animals treated intravenously with pentamidine.

All four aromatic amidoximes tested were active against *P. carinii* when administered orally by gavage once daily for 14 days (see Table 2). Mean cyst counts for each test group were significantly reduced compared to the saline control group. Compounds 3, 5 and 7 were most active. The aromatic diamidines corresponding with the amidoximes 3, 5, and 7 (compounds 4,6 and 8, respectively), in contrast, had reduced or no anti-*P. carinii* activity when given orally (see Table 3). The only diamidine with significant oral activity was compound 8. Its corresponding diamidoxime (compound 7) was more active (see Table 2).

All aromatic amidoximes tested had excellent anti-*P. carinii* activity when given intravenously. Mean cyst counts for Compounds 1, 3, 5, and 7 were significantly reduced compared to saline controls (see Table 2), and were also lower than cyst counts for the intravenous pentamidine group. The diamidine compounds 4, 6, and 8 were previously shown to have intravenous activity (see Table 3). Direct comparisons of diamidine and corresponding diamidoxime (Compounds 3, 5, 7) intravenous activities cannot be made, however, as the intravenous activities of diamidines were previously evaluated by a different score method and at slightly different doses. However, the data indicates that the amidoximes compare favorably with regard to intravenous efficacy.

EXAMPLE 5

Novel Compounds of Formula II: Antipneumocystic Activity and Toxicity

It has been reported that 2,5-bis-[4-amidinophenyl]furan (compound 9) is more active and less toxic than pentamidine against *Pneumocystis carinii* in the immunosuppressed rat model on intravenous dosage. D. W. Boykin et al., *J. Med. Chem.* 38, 912 (1995). However, the activity of 9 in the rat model was significantly less on oral administration.

The aromatic amidoxime derivatives of compound 9, listed above as compounds 10, 11, and 12, were prepared according to a two-step process using Pinner methodology to convert a nitrile to an imidate ester, followed by reactions of the imidate ester with hydroxylamine. A. Pinner, Ber. 17, 184 (1884).

Table 4 provides the results of evaluation of the prodrugs 10, 11, and 12, administered as dimaleinate salts, against *P.*

*carinii* pneumonia in the immunosuppressed rat model (see Example 4) on both oral and intravenous administration. Data from compound 9 are provided for comparison purposes. In Table 4 the following legend is applicable in interpreting the data:

$^a$ dosage by tail vein injections $^b$ subjective scale of toxicity. See R. R. Tidwell, et al., *Antimicrob. Agents Chemother.* 37, 1713 (1993). In general, the larger the value the more severe the toxicity, with values greater than 2 indicating the death of some animals $^c$ cysts counted in lung tissue employing a blinded protocol, and reported as a percentage of the saline treated controls. See R. L. Lombardy et al., *J. Med. Chem.* 39, 1452 (1996).

$^d$ oral dosage by gavage $^e$ dosage by tail vein injection $^f$ not available, experiment suspended on day 8 due to severe necrosis of the tail at the injection site $^g$ compounds administered as the dimaleinate salt The results shown in Table 4 demonstrate that compounds 10 and 11 are effective when given orally by gavage, as compared to the saline control. The data also show that the amidoximes can function as prodrugs in the furan series. The values for the cyst counts suggest that drug uptake on oral dosage for 10 and 11 are superior to that of the parent compound 9. Unexpectedly, the bis-O-methylamidoxime 11 is more effective than the bis-amidoxime 10.

On intravenous administration of both 10 and 11, the acute toxicity generally noted for diamidines was absent. However, for compound 10, considerable inflammation and necrosis of the tail vein at the injection site is observed even at the relatively low dosage of 5.5 μmol/day. In contrast, the bis-O-methylamidoxime 11 is well-tolerated, as inflammation and necrosis at the injection site are absent even with intravenous administration of 22.0 μmol/kg/day.

EXAMPLE 6

Reduced Acute Toxicity of Amidoximes of Formula I in Normal Rats

Toxicity was studied in rats that were not immunosuppressed by dexamethasone treatment. Adult male Sprague-Dawley rats, barrier raised, not certified virus free, and weighing 300 to 450 g at the time, were obtained from Hilltop Laboratories (Scottsdale, Pa.) The individually caged animals were given water and rat chow (Agway, Syracuse, N.Y.) ad libitum. Each animal was injected via the tail vein with one dose of test compound. Animals were observed closely for a 10 to 12-minute period following injection of the test drug each day for signs of acute toxicity, including the hypotensive response (paling of eyes and paws, dyspnea, lethargy and decreased body temperature) elicited by intravenous pentamidine at its effective dose. See R. R. Tidwell et al., *J. Protozool.* 36, 74S–76S (1989); R. R. Tidwell et al., *J. Med. Chem.* 33,1252 (1990)). Each animal was closely observed for 15 min post-injection, and monitored again at 30 min., 60 min. and 24 hr. post-injection. The rats' health and general well-being were observed and recorded on a daily basis for the remainder of the experiment. Excessive weight loss (a greater than 25 g weight loss over the two-week dosing period was considered excessive in comparison with saline controls) was considered a key indicator of declining health due to drug toxicity. At necroscopy, the liver, spleen, kidneys and pancreas were removed from each animal, examined for gross pathology, and saved for histopathology.

In these normal rats, overt acute adverse reactions following single intravenous injections were greatly reduced for three bis-benzamidoximes (compounds 1, 5, and 7) as compared to the bis-benzamidines (compounds 2 (pentamidine), 6, and 8). No adverse reactions were observed after very high single oral doses of the bis-benzamidoximes. To compare, normal rats injected over a 30-second period with 20 μmol/kg pentamidine appeared hypotensive, with rapid paling of extremities, hypoactivity and dyspnea, which progressed to slight cyanosis of extremities. Increased lacrimation and minor hind leg ataxia were observed immediately before onset of hypoactivity. The animals appeared to recover within 5 minutes after injection. Animals injected with 40 μmol/kg pentamidine had immediate sever hind limb contractions, increased salivation, dyspnea, initial paling of extremities which progressed to marked cyanosis and profound hypoactivity, with no movement for at least 5 minutes. The animals appeared to recover approximately 20 minutes after injection. In contrast, the diamidoxime analog of pentamidine (compound 1), given in the same manner, caused no observable adverse reactions from 20 to 60 μmol/kg. Minor toxic responses, including barely observable hindleg ataxia and slight hypoactivity, were observed at 80 μmol/kg, with complete recovery at 5 minutes post-injection. Bolus injections above 120 μmol/kg produced severe dyspnea and profound hypoactivity.

Similar results were observed for diamidoxime compounds 5 and 7 compared with their respective diamidine analogs. The diamidine compound 6 appeared less acutely toxic than pentamidine, with no overt toxicity at 20 μmol/kg. Dyspnea progressing to cyanosis, excessive salivation and lacrimation, and hypoactivity, were observed at 40 μmol/kg. These responses became more severe at 80 and 100 μmol/kg, with symptoms persisting for 30 minutes after injection. The diamidoxime compound 5, in contrast, caused no overt toxicity at 20, 40 or 80 μmol/kg, and only minor ataxia and/or hypoactivity at the high dose of 160 μmol/kg. Animals had fully recovered at 5 minutes after injection.

The diamidine compound 8 appeared even more acutely toxic than the other two diamidines tested, with perceptible hypoactivity occurring in animals dosed at 10 μmol/kg. Strong muscular contractions and tremors, extensive salivation and lacrimation, dyspnea and marked hypoactivity, which persisted for longer than 15 minutes, were observed in animals injected with 20 μmol/kg. In contrast, animals injected with the diamidoxime analog, compound 7, showed no observable adverse effects at 20 or 40 μg/kg and only very minor hypoactivity and dyspnea at 80 μmol/kg, with recovery at 5 minutes. Compound 7 injected at 160 μmol/kg caused pronounced hypoactivity, dyspnea, cyanosis, and increased salivation and lacrimation, with symptoms persisting for approximately 10 minutes after injection.

No overt toxic responses were seen when the rats were given any of the test compounds orally, including single oral doses as high as 160 μmol/kg for each of the diamidoxime compounds 1, 5, and 7.

EXAMPLE 7

In vitro Metabolism of Compounds of Formula I

In vitro metabolism of diamidoximes 1, 3, 5, and 7 by rat liver homogenate 9000×g supernatants, post-mitochondrial 105,000×g supernatants or microsomal fractions were performed as previously described in B. J. Berger et al., *Antimicrob. Agents and Chemotherapy* 36, 1825–1831

(1992); B. J. Berger et al., *J. Pharmacol. Experimental Therapeutics* 256, 883-89 (1991). Briefly, adult male Sprague-Dawley rats, barrier raised, (Hilltop Laboratories, Scottsdale, Pa.) animals were given water and rat chow (Agway, Syracuse, N.Y.) ad libitum. The rats were euthanized by decapitation, the livers removed immediately, rinsed with 50 mM potassium phosphate buffer, pH 7.4, and placed on ice. All subsequent steps were performed at $4_E$C. The livers were minced, homogenized, and 9000×g supernatants, 105,000×g or 105,000×g microsomal pellets prepared. Each fraction was assayed for protein content as described in M. M. Bradford, *Anal. Biochem.* 72, 248–254 (1976) and stored at $-80_E$C. Fractions from the rat kidneys, lungs, hearts and brains were prepared similarly.

Reaction mixtures consisted of 1.5 mL 50 mM potassium phosphate buffer, pH 7.4, 0.5 mL cofactor solution (2 mg/mL NADPH, 1.6 mg/mL MgCl2, 1.04 mg/mL glucose-6-phosphate and 2 units/mL glucose-6-phosphate dehydrogenase in 50 mM potassium phosphate buffer pH 7.4), 0.5 mL tissue homogenate and 0.5 mL of the appropriate diamidoxime substrate at a concentration of 167 $\mu$M. Reactions were started by adding substrate, then mixtures were incubated at $37_E$C in a shaking water bath for times shown in the figures. Reactions were terminated by extracting over $C_{18}$ cartridges and assaying as described below.

Metabolic experiments with intact cultured cells were performed using the BRL 3A hepatocyte line, obtained from the UNC-Chapel Hill Lineberger Tissue Culture Facility. Cells were routinely cultured in Costar (Cambridge, Mass.) 25 $cm^2$ of tissue culture flasks at $37_E$C under moist 5% $CO_2$ and 95% air in Ham's F-12 medium (Gibco, Gaithersburg, Md.) containing 5% fetal bovine serum (HyClone Laboratories Inc., Logan, Utah). Confluent cultures were treated with 0.25% trypsin solution (Sigma Chemical Co., ST. Louis Mo.), then approximately $2 \times 10^5$ cells/well subcultured into Costar 6-well tissue culture chambers and the cells allowed to grow to confluency. Ten mL fresh medium was added to each culture well and incubations were started by adding 100 $\mu$L amidoxime solution (prepared in sterile water) to a final concentration of 10 $\mu$M. Cell cultures were incubated at $37_E$C under moist 5% $CO_2$ and 95% air for 24 hours, then aliquots of culture supernatants extracted and assayed for metabolites as described below. Similar metabolic experiments were performed with cultured J774 A.1 mouse monocyte-macrophage cells cultured in DMEM F-12 medium containing 10% fetal bovine serum and H9c2 rat heart myoblast cells cultured in DMEM H medium containing 10% fetal bovine serum.

Samples were extracted using solid phase extraction and assayed using high performance liquid chromatography (HPLC) by methods similar to those previously described in Berger et al. (1992) and Berger et al., (1991), supra. Briefly, samples spiked with 2,5-bis[4-(N-isopropylamidino)phenyl] furan dihydrochloride as the internal standard (IS) were extracted over activated $C_{18}$ Bond Elut cartridges (Varian Associates, Sunnydale, Calif.), washed with water, 100% acetonitrile, then eluted with 75% acetonitrile/25% water containing 15 mm triethylamine and 35 mM acetic acid. The diamidoxime substrates elute in the 100% acetonitrile phase, while mono-amidine and diamidine products elute in the acetonitrile/water mixture containing triethylamine and acetic acid. Elutes were evaporated to dryness at $40_E$C under a gentle stream of nitrogen and resuspended in HPLC grade water.

Compounds were resolved using a Hewlett-Packard (Avondale, Pa.) model 1090 HPLC equipped with a HP 1050 variable wavelength detector set at 265 nm, a 4.6×250 mm Zorbax RX diisopropyl C8 column (Mac-Mod, Chadd's Ford, PA) maintained at $40_E$C and a Vectra 486/66U computer with HP Chemstations software. The mobile phase consisted of 15 mM triethylamine and 35 mM acetic acid in HPLC grade water for pump A, and 15 mM triethylamine and 35 mM acetic acid in 75% acetonitrile in water for pump B. The solvent flow rate was 1.5 mL/min, and the solvent gradient ran from 0% B to 25% B at 22 min, to 40% B at 25 min, then 90% B at 35 min. All solvents and reagents used for the assays were HPLC grade. Quantities of metabolites formed were calculated, using peak area rations of authentic standard, from standard addition curves generated by spiking standards into tissue homogenates or tissue culture medium.

It has been shown that rat liver homogenate 9000×g supernatants readily reduce the diamidoxime analog of pentamidine (compound 1), forming large quantities of the monoamidine-monoamidoxime derivative, and smaller amounts of pentamidine (compound 2). B. Clement et al., *Drug Metabol. Dispos.* 22, 486-97 (1994); see FIG. 1A. The metabolites have been previously identified by mass spectrometry. U. Bronner et al., *Pharmacol. Toxicol.*, 77, 114-20 (1995). The bis-benzamidoximes of the present invention (compounds 3, 5, and 7), appear to be metabolized similarly by rat liver homogenate 9000×g supernatants, as shown in FIGS. 1B, 1C, and 1D, respectively. In each case, two new product peaks were eluted. The smaller peaks in FIGS. 1B, 1C, and 1D coeluted with the diamidine standard compound 4, 6, and 8, respectively. Although synthetic standards are not available for the monoamidine/monoamidoxime derivatives of compounds 3, 5, and 7, the relative retention times of the chromatographic peaks are entirely consistent with those predicted for the monoamidoxime derivatives.

Figure 2:
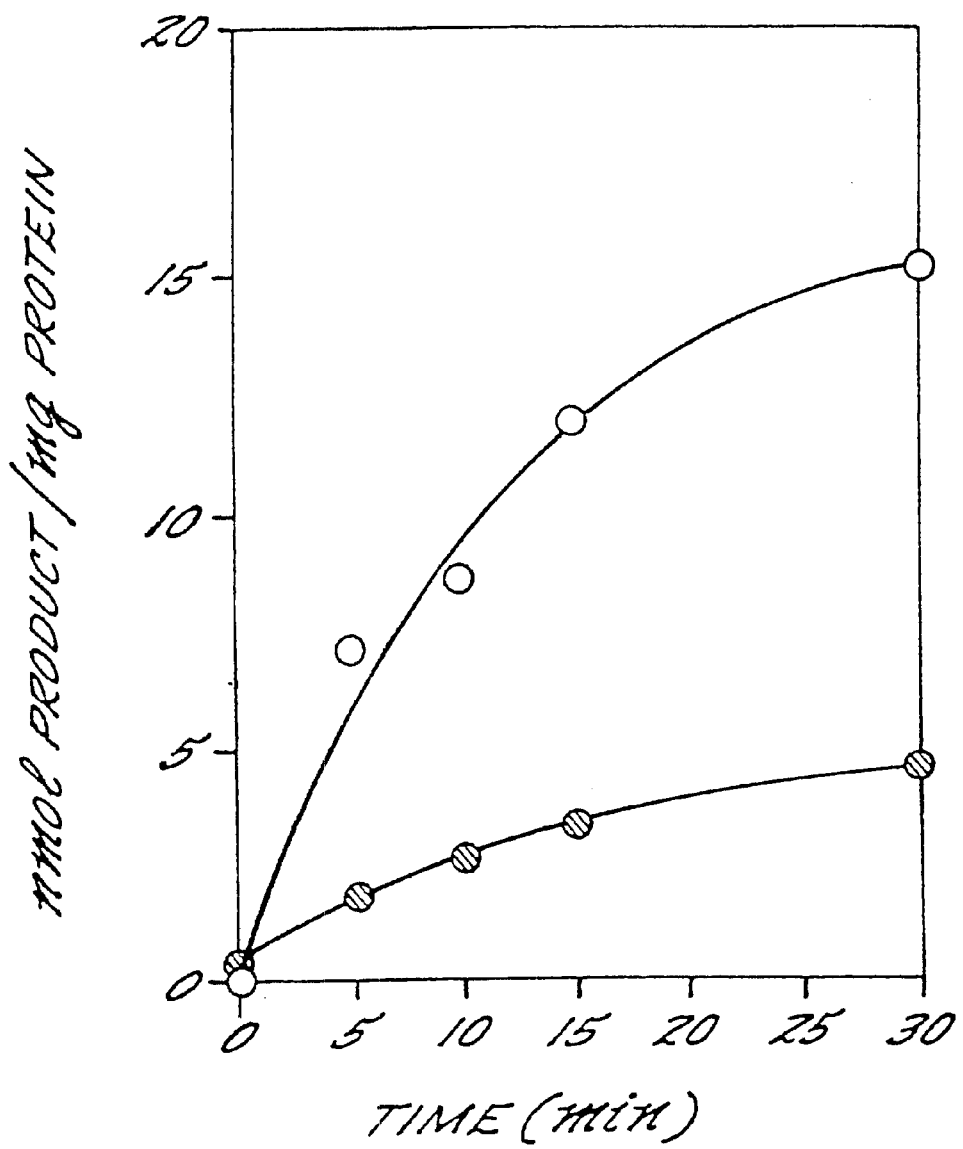
FIG. 2 is a graphical illustration of the time course of reduction of bis-benzamidoxime compound 1 to its monoamidine-monoamidoxime product expressed by the measure of nmol of product/mg of protein (y-axis value) as a function of time in minutes (x-axis value). The open circles represent data points for the reduction of compound 1 in the rat liver post-mitochondrial supernatant fraction described below in Example 7. The closed circles represent data points for the reduction of compound 1 in the rat liver microsomal fractions, also described in Example 7.
Figure 3:
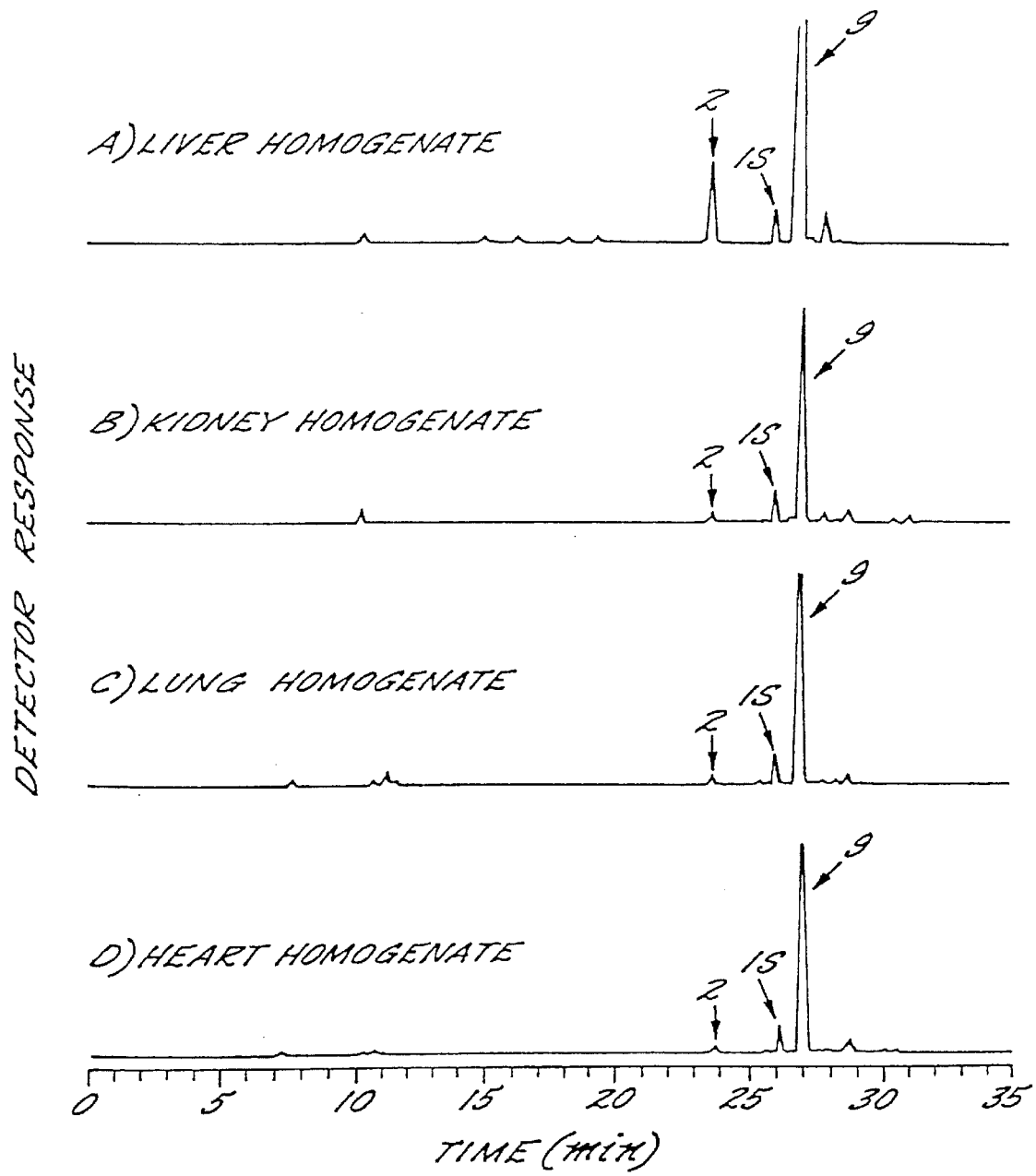
FIG. 3 is a spectral illustration of the metabolism of bis-benzamidoxime compound 1 into its amidine analog pentamidine (indicated in the Figure by the numeral 2) and its monoamidine-monoamidoxime derivative (indicated in the Figure by the numeral 9) by the 9000×g supernatants of homogenates of rat liver (FIG. 3A); rat kidney (FIG. 3B); rat lung (FIG. 3C) and rat heart (FIG. 3D).

The N-hydroxylation of aromatic amidines to form aromatic amidoximes is known to be catalyzed by specific cytochromes P450. See B. Clement et al., *Drug Metabol. Dispos.* 22, 486-97 (1994). However, reduction of amidoximes back to the amidines has been reported to be catalyzed by a non-cytochrome P450 dependent reductase activity. Id. The data presented in FIGS. 2 and 3 indicate that reductase is present in the post-mitochondrial microsomal fraction. However, reductase activity appears to be even higher in the post-mitochondrial supernatant fraction (FIG. 2). The results also show that high reductase activity is also found in homogenates from rat kidneys and lung, as well as from heart and brain (FIG. 3). The latter tissues are known to contain little cytochrome P450 activity.

Figure 4:
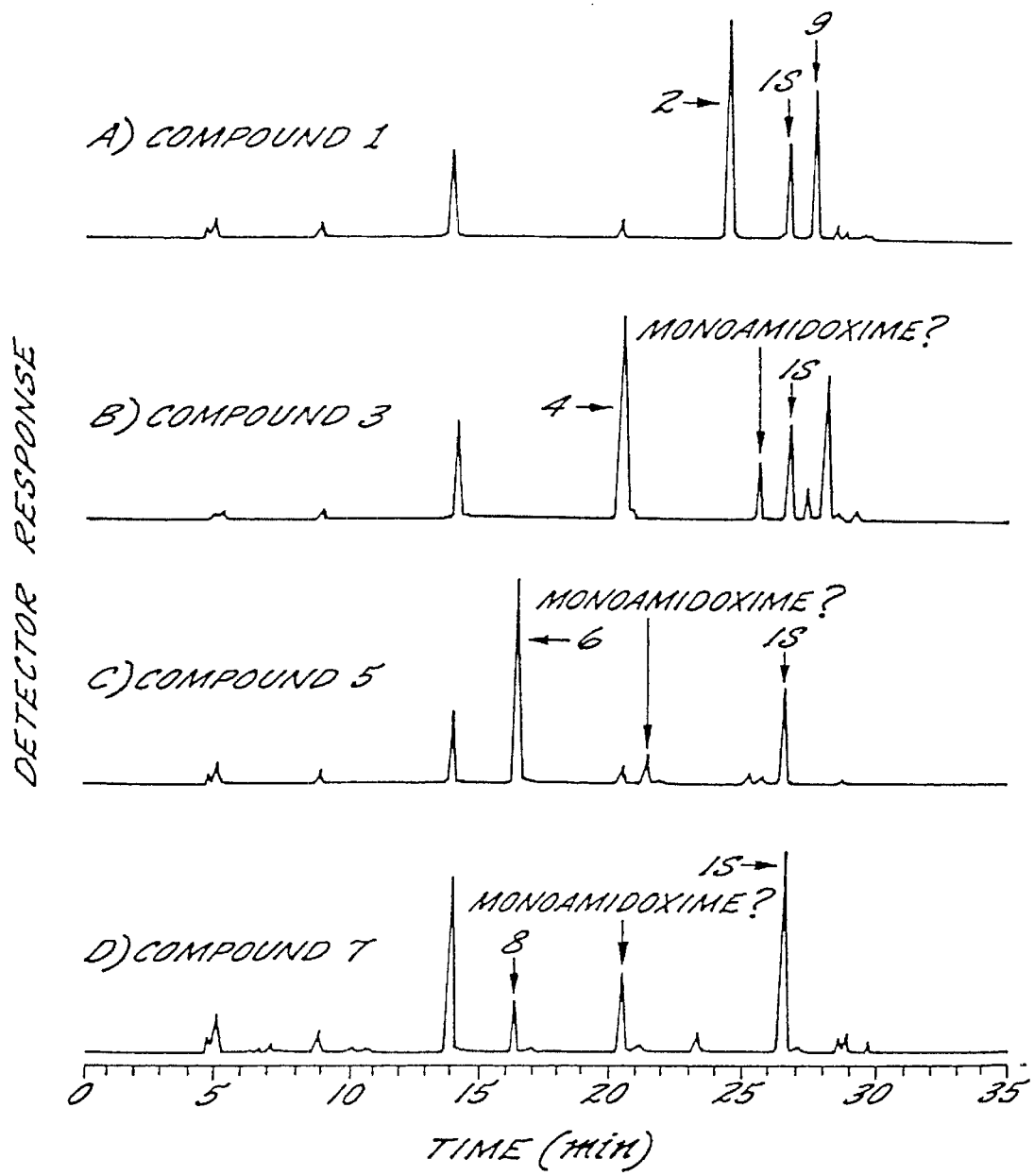
FIG. 4 is a spectral illustration of the metabolism of bis-benzamidoximes of the present invention in intact BRL 3A hepatocytes in vitro. In the metabolism studies illustrated in FIGS. 4A, 4B, 4C, and 4D, cells cultured in Ham's F-12 medium containing 5% fetal bovine serum and 10 $\mu$M diamidoxime substrate were incubated for 24 hours at $37_E$C under 5% $CO_2$. The extracellular medium was extracted and then assayed by HPLC as described below in Example 7. In all Figures, "IS" means internal standard.

Finally, intact cells of the established liver cell line BRL 3A (FIG. 4), the heart cell line H9c2 (data not shown) and the macrophage cell line J774 A.1 (data not shown) all readily absorbed and metabolized the diamidoxine compounds. These data indicate that metabolism of amidoxime prodrugs is catalyzed by activities other than cytochromes P450, and demonstrate that tissues and other cells other than liver possess high levels of activity. It appears that in order for diamidoxime prodrugs to be effective against extracellular parasites such as *P. carinii*, the compounds must apparently enter the host cells, be chemically reduced back to the active amidine analog, then released extracellularly and taken up by the infectious organism. The process of cell uptake, metabolism, and release, occurs readily in BRL 3A hepatocytes cultured in vitro (FIG. 4). Each of the orally active bis-benzamidoximes 1, 3, 5, and 7 were metabolized predominantly to the corresponding diamidine, which was then released in high concentrations back into the culture supernatants.

TABLE 2

Activity of aromatic amidoximes against *Pneumocystis carinii* pneumonia.

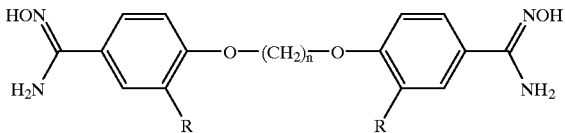

| Compound | n | R | ORAL DOSING[a] cysts/g lung ∀ S.E.(× 10⁶) | % saline | # rats | IV DOSING[b] cysts/g lung ∀ S.E.(× 10⁶) | % saline | # rats |
|---|---|---|---|---|---|---|---|---|
| Saline | — | — | 37.78 ∀ 9.49 | 100.00 | 6 | 32.36 ∀ 11.03 | 100.00 | 6 |
| Pentamidine | — | — | 50.28 ∀ 15.20 | 133.09 | 6 | 0.28 ∀ 0.08[c] | 0.87 | 6 |
| 1 | 5 | H | 7.28 ∀ 5.22[c] | 19.27 | 5 | 0.05 ∀ 0.01[c] | 0.15 | 6 |
| 3 | 4 | H | 0.54 ∀ 0.23[c] | 1.43 | 5 | 0.04 ∀ 0.02[c] | 0.12 | 6 |
| 5 | 3 | H | 0.85 ∀ 0.36[c] | 2.25 | 5 | 0.01 ∀ 0.003[c] | 0.03 | 6 |
| 7 | 3 | OCH$_3$ | 1.40 ∀ 1.18[c] | 3.71 | 6 | 0.01 ∀ 0.002[c] | 0.03 | 3 |

[a]Oral doses administered daily for 14 days by gavage @33 μmol/kg body weight.
[b]Intravenous doses administered daily for 14 days by tail vein injection at 22 mg/kg body weight.
[c]Significantly different from saline control group ($P < 0.05$); Student's test.

TABLE 3

Activity of aromatic amidines against *Pneumocystis carinii* pneumonia.

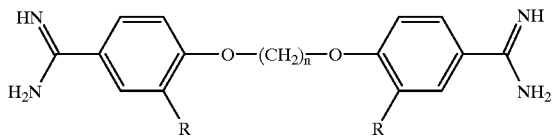

| Compound | n | R | ORAL DOSING[a] cysts/g lung ∀ S.E. × 10⁶ | % saline | # rats | IV DOSING[b] mean histological score[c] | # rats |
|---|---|---|---|---|---|---|---|
| Saline | — | — | 37.78 ∀ 9.49 | 100.00 | 6 | 3.2 | 72 |
| Pentamidine | 5 | H | 50.28 ∀ 15.20 | 133.09 | 6 | 1.1 | 63 |
| 4 | 4 | H | 17.39 ∀ 7.03 | 46.03 | 6 | 0.5 | 8 |
| 6 | 3 | H | 16.43 ∀ 6.36 | 43.49 | 6 | 0.9 | 8 |
| 6 | 3 | OCH$_3$ | 3.20 ∀ 0.58 | 8.47 | 6 | 0.6 | 8 |

[a]Oral doses administered daily for 14 days by gavage @33 μmol/kg body weight.
[b]Intravenous doses administered daily for 14 days by tail vein injection @ 10 mg/kg body weight. Compound 10 given at 5 mg/kg.
[c]Data reprinted from J. Med. Chem. 33:1252 (1990). The histological score was determined subjectively from cysts detected in stained lung sections. Scores range from a low infection score of 0.5 to a high of 4.0.

TABLE 4

Activity of prodrugs of Bis-2,5-[4-Amidophenyl]furan against *Pneumocystis carinii* pneumonia.

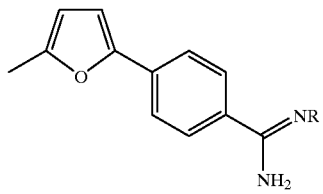

| Compound | R | ORAL DOSING | | | IV DOSING | | |
|---|---|---|---|---|---|---|---|
| | | Dosage[a] (μmol/kg/day) | Toxicity[b] | cysts in lung tissue[c] | Dosage[d] (μmol/kg/day) | Toxicity | Cysts in Lung tissue |
| saline | — | not done | | | | 0 | 100.0 ∀ 9.51 |
| 2[e] | — | not done | | | 22.0 | +2 | 3.94 ∀ 1.49 |
| 9[g] | H | 66.3 | 0 | 25.2 ∀ 9.84 | 26.6 | +1 | NA[f] |
| | | 39.8 | 0 | 42.3 ∀ 12.6 | 13.3 | 0 | 0.79 ∀ 0.34 |
| | | | | | 2.7 | 0 | 7.26 ∀ 3.56 |
| | | | | | 0.3 | 0 | 6.92 ∀ 3.36 |
| | | | | | 0.03 | 0 | 26.3 ∀ 5.0 |
| 10[g] | OH | 33.0 | 0 | 3.1 ∀ 1.31 | 22.0 | +1 | 0.67 ∀ 0.46 |
| | | 11.0 | 0 | 197.6 ∀ 64.4 | 11.0 | +1 | 1.37 ∀ 0.61 |
| | | 5.5 | 0 | 127.0 ∀ 48.4 | 5.5 | +1 | 42.3 ∀ 34.4 |
| | | | | | 2.7 | 0 | 54.4 ∀ 27.4 |
| | | | | | 0.3 | 0 | 203.6 ∀ 56.4 |
| 11[g] | OCH$_3$ | 33.0 | 0 | 1.82 ∀ 0.53 | 22.0 | 0 | 14.3 ∀ 5.14 |
| | | 22.0 | 0 | 12.0 ∀ 11.5 | | | |
| | | 11.0 | 0 | 34.7 ∀ 21.2 | | | |
| | | 5.5 | 0 | 264.2 ∀ 72.9 | | | |
| 12[g] | OCH$_2$CH$_3$ | 33.0 | 0 | 121.5 ∀ 48.4 | 22.0 | +1 | 104.7 ∀ 49.9 |

The foregoing is illustrative of the present invention and is not to be construed to be limiting thereof. The invention is defined by the following claims, with equivalents of the claims to be included herein.

That which is claimed is:

1. A method of treating a microbial infection in a subject in need of such treatment, comprising orally administering to said subject a compound, wherein said compound is a bis-benzamidoxime that is reduced in said subject to produce a benzamidine having anti-*Pneumocystis carinii* activity.

2. The method according to claim 1, wherein said microbial infection is caused by a microbe selected from the group consisting of fungi, algae, bacteria, and viruses.

3. A method according to claim 1, wherein the bis-benzamidoxime is a compound of Formula I or a pharmaceutically acceptable salt thereof:

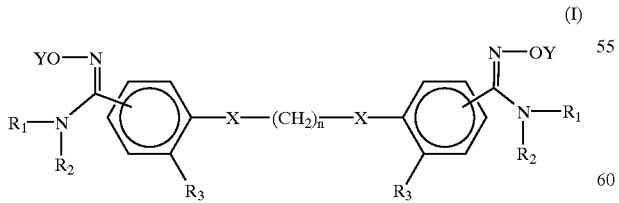

(I)

wherein:

$R_1$ and $R_2$ are each independently selected from the group consisting of H, lower alkyl, oxyalkyl, alkoxyalkyl, cycloalkyl, aryl, hydroxyalkyl, aminoalkyl or alkylaminoalkyl;

$R_3$ is H, loweralkyl, oxyalkyl, alkoxyalkyl, hydroxyalkyl, cycloalkyl, aryl, aminoalkyl, alkylaminoalkyl or halogen;

n is from 2 to 6;

X is O or S; and

Y is H or lower alkyl.

4. The method according to claim 3, wherein said compound is a maleinate salt of a compound of Formula I.

5. The method according to claim 3, wherein n is 3 or 4; X is O; Y is H; $R_1$ and $R_2$ are each H; and $R_3$ is H or —OCH$_3$.

6. The method according to claim 1, wherein the bis-benzamidoxime is a compound of Formula II or a pharmaceutically acceptable salt thereof:

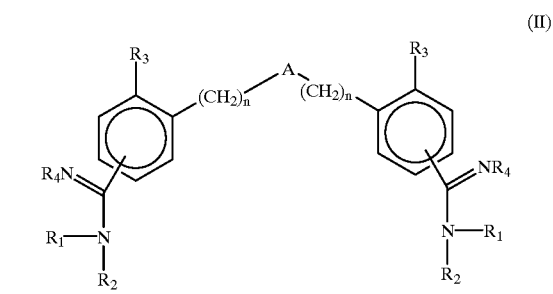

(II)

wherein:

R$_1$ and R$_2$ are each independently selected from the group consisting of H, loweralkyl, oxyalkyl, alkoxyalkyl, cycloalkyl, aryl, hydroxyalkyl, aminoalkyl or alkylaminoalkyl;

R$_3$ is H, loweralkyl, oxyalkyl, alkoxyalkyl, hydroxyalkyl, cycloalkyl, aryl, aminoalkyl, alkylaminoalkyl or halogen;

R$_4$ is —OY, or R$_1$ to and R$_4$ together represent

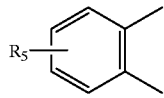

wherein R$_5$ is

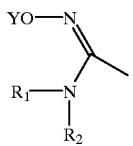

and Y is H or loweralkyl;

n is an integer from 0 to 2; and

A is a heterocyclic aromatic group selected from the group consisting of:

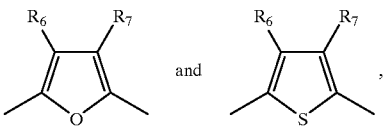

wherein R$_6$ and R$_7$ are each independently selected from the group consisting of H, loweralkyl, halogen, oxyalkyl, oxyalkyl, oxyaryl, or oxyarylalkyl.

7. The method according to claim 6, wherein n is 0;

A is

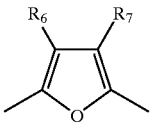

R$_4$ is —OY;

and R$_1$, R$_2$, R$_3$, R$_5$ and R$_6$ are each H.

8. The method according to claim 1, wherein said subject is afflicted with a microbial infection.

9. The method according to claim 1, wherein said subject is at risk of developing a microbial infection and said compound is administered in a prophylactically effective amount.

* * * * *